United States Patent [19]
Hayashi

[11] Patent Number: 5,182,453
[45] Date of Patent: Jan. 26, 1993

[54] ION SCATTERING SPECTROMETER

[75] Inventor: Shigeki Hayashi, Kyoto, Japan

[73] Assignee: Shimadzu Corporation, Kyoto, Japan

[21] Appl. No.: 836,384

[22] Filed: Feb. 18, 1992

[30] Foreign Application Priority Data

Feb. 22, 1991 [JP] Japan .................................. 3-103681
Feb. 22, 1991 [JP] Japan .................................. 3-103682

[51] Int. Cl.$^5$ ............................................ H01J 37/252
[52] U.S. Cl. ..................................... 250/309; 250/305
[58] Field of Search ................................ 250/309, 305

[56] References Cited

U.S. PATENT DOCUMENTS 4,100,409  7/1978  Brongersma ........................ 250/305
5,068,535  11/1991  Rabalais ............................. 250/309

FOREIGN PATENT DOCUMENTS 63-102150  5/1988  Japan ................................. 250/309

OTHER PUBLICATIONS

English Abstract of Japanese Laid-Open (Kokai) Patent Application No. 59-66043.

Primary Examiner—Jack I. Berman
Attorney, Agent, or Firm—Oliff & Berridge

[57] ABSTRACT

In a coaxial impact collision ion scattering spectrometer (CAICISS), a Wien filter composed of a pair of electrodes 13 and a magnet 20 is placed in the flying path of the ions. The Wien filter acts as (a) a chopper for intermittently chopping ion beam irradiated onto the sample 17, and as (b) a filter that directs only ions having predetermined mass and electrical charges toward an aperture 16 and deviates other ions or non-ionized atoms from the aperture 16. Thus non-ionized atoms or impurity ions having different mass or electric charge are prevented from irradiating the sample 17. In another CAICISS, the axis A of the ion source 11 is set oblique to the axis B of the ion beam irradiated onto the sample 14, and only ions having predetermined mass and electrical charges are deflected from the axis A to the axis B by a pair of deflecting electrodes 13.

8 Claims, 2 Drawing Sheets

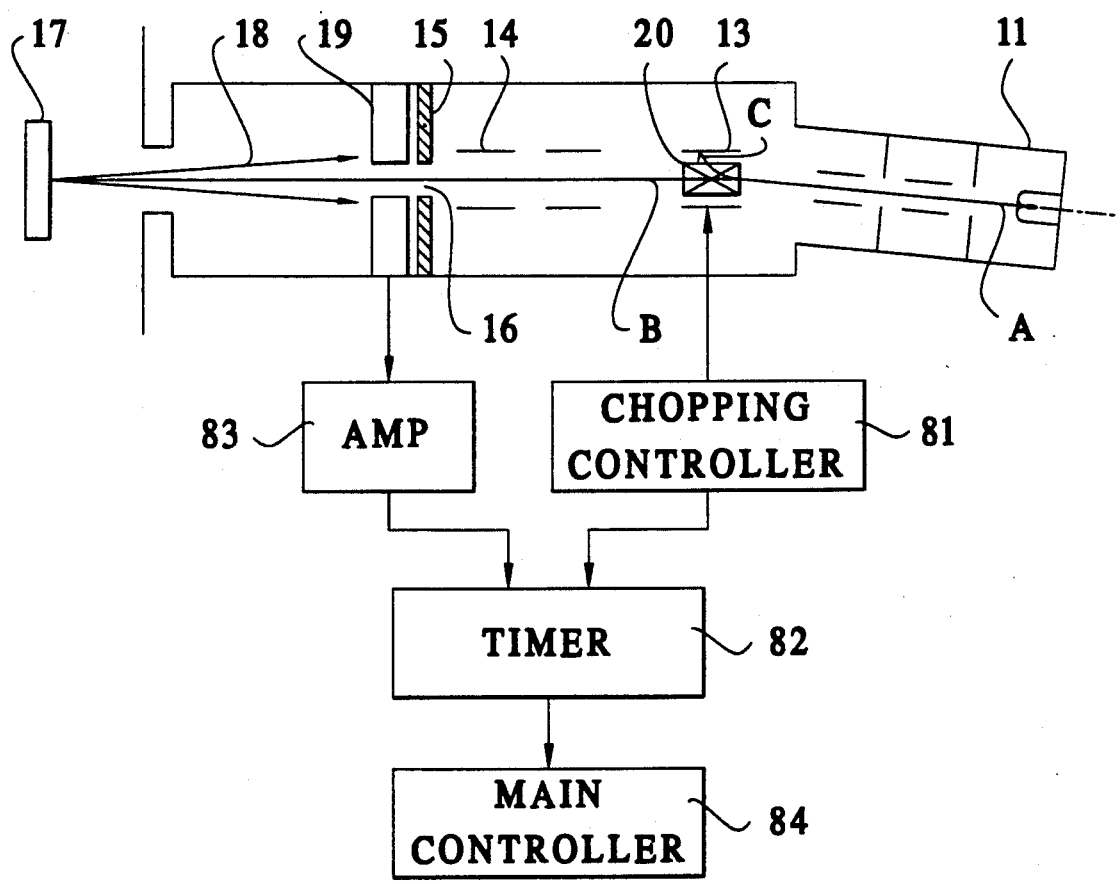

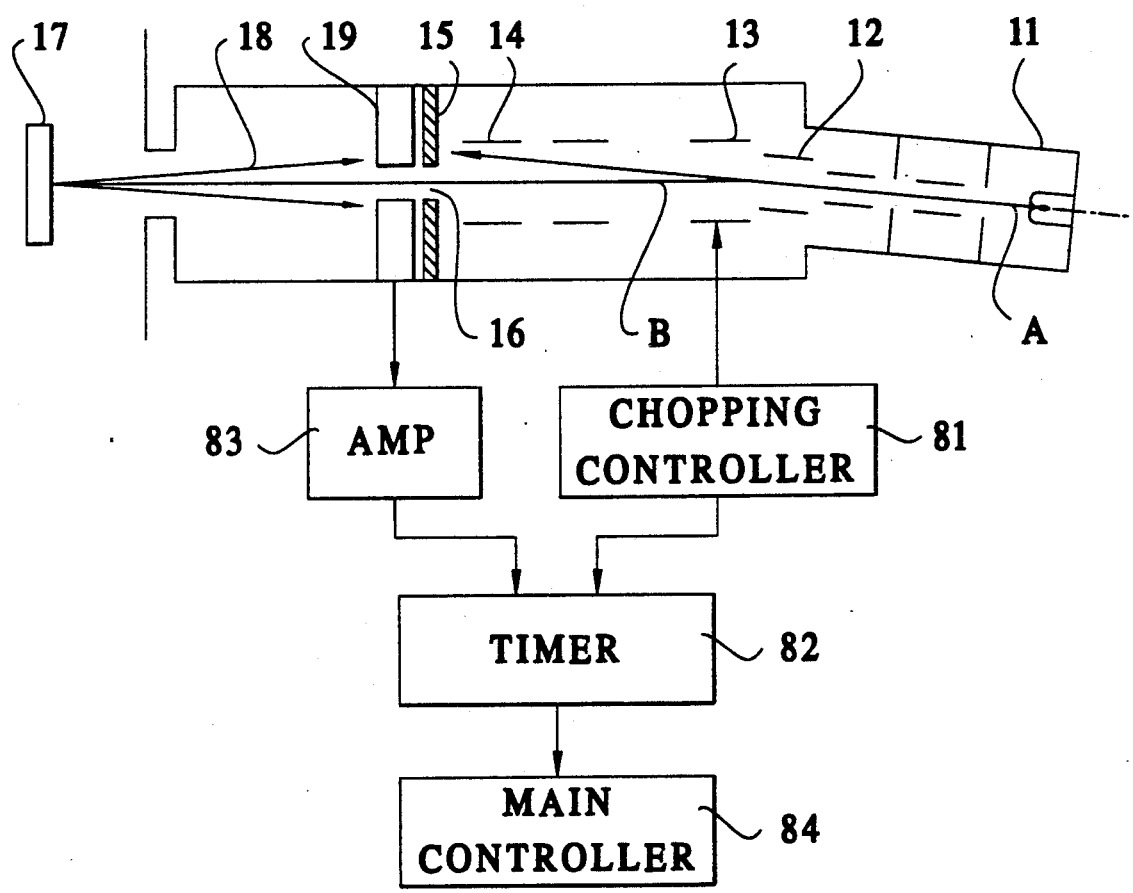

ION SCATTERING SPECTROMETER

The present invention relates to ion scattering spectrometers (ISS), especially coaxial impact collision ion scattering spectrometers (CAICISS), in which ions are irradiated onto a sample and the back-scattered ions are observed to analyze the surface of the sample.

BACKGROUND OF THE INVENTION

Coaxial impact collision ion scattering spectrometers (CAICISS) are widely used in researching semiconductors and new materials to analyze chemical composition or crystalline structure of a sample especially in its surface.

In a CAICISS, a beam of ions having known mass and known speed (that is, known kinetic energy) is irradiated from an ion source onto a sample. The irradiated ions elastically collide with the atoms of the sample mostly in its surface and are scattered, when the scattered ions lose a part of their energy depending on the mass of the collided atom in the sample surface. Among the scattered ions, those scattered backward are detected by an ion detector placed in the same direction as the ion source in relation to the sample surface (that is, the ion source and the ion detector are placed coaxial). By measuring the energy of the back-scattered ions, the surface of the sample can be analyzed. In a time-of-flight type CAICISS, the energy of the back-scattered ions is measured by their speed, and the speed is measured by the time of flight until the ions are detected by the ion detector.

Here it is apparent that the correct analysis of the sample needs the exact knowledge of the mass and energy of the irradiated ions. The ions irradiated onto the sample are generated in the ion source by ionizing a source gas. One of the problems of prior art CAICISSs is neutral atoms included in the ions irradiated onto the sample. While not all the source gas is ionized in the ion source, the non-ionized atoms come out of the ion source by the thermal motion. Prior art CAICISSs have a straight path from the ion source to the sample surface and the ion beam continuously ejected from the ion source is chopped by chopping electrodes, whereby the ions are intermittently irradiated onto the sample and the time of flight is measured distinctly. Since the non-ionized atoms are electrically neutral, they are not chopped by the chopping electrodes but are continuously irradiated onto the sample.

Another problem is impurity ions inevitably included in the ions generated in the ion source. When the source gas is ionized, residual gas in the ion source, impurity gas in the source gas, or vapor gas from a heater filament are also ionized. In prior art CAICISSs, all the ions including such impurity ions are ejected from the ion source and irradiated onto the sample.

In these cases, the energies of the impurity ions or neutral atoms irradiated onto the sample are unknown, whereby the impurity ions and neutral atoms scattered by the sample surface and detected by the detector make noise and build higher background in detection signals of the ion detector.

SUMMARY OF THE INVENTION

An object of the present invention is to provide a CAICISS in which impurity ions and neutral atoms included in the ions coming out of the ion source are adequately eliminated and the accuracy and sensitivity of the measurement is enhanced.

Thus an ion scattering spectrometer according to the present invention includes:
a) an ion source for ejecting ions on a first axis;
b) a Wien filter placed on the first axis and including
   a pair of electrodes for producing an electric field with the direction non-parallel to the first axis and
   a magnet for producing a magnetic field with the direction non-parallel to the first axis and to the direction of the electric field;
c) a chopping controller for intermittently adjusting the electric field and/or the magnetic field to deflect the ions from the first axis to a second axis; and
d) an aperture plate placed on the second axis between the Wien filter and the sample, and having an aperture at the intersection of the aperture plate and the second axis, whereby the ions are intermittently irradiated onto the sample and otherwise prevented by the aperture plate.

Another type of ion scattering spectrometer according to the present invention includes:
a) an ion source for ejecting ions along a first axis;
b) a deflector for deflecting ions having a predetermined mass and electric charge toward a second axis which intersects the first axis;
c) an aperture plate placed intersecting the second axis and having an aperture at the intersecting point for allowing the ions deflected by the deflector to be irradiated onto the sample and preventing other ions;
d) a pair of chopping electrodes for intermittently allowing the ions to pass through the aperture;
e) a detector for detecting ions scattered backward by the sample; and
f) a timer for measuring the time for which the ions fly from the chopping electrodes to the detector.

Detail of the structure and the operation of the invention with other important features is described in the description of preferred embodiments that follows.

BRIEF DESCRIPTION OF THE DRAWINGS

FIG. 1 is a schematic cross-sectional view of a CAICISS embodying the present invention.

FIG. 2 is a schematic cross-sectional view of another CAICISS embodying the present invention.

DETAILED DESCRIPTION OF PREFERRED EMBODIMENTS

A time-of-flight type CAICISS as the first embodiment of the present invention is shown in FIG. 1. When a sample 17 is analyzed, the CAICISS is set so that the axis B of the CAICISS (along which the ion beam is ejected) is set perpendicular to the surface of the sample 17. In the CAICISS of the present embodiment, the axis A of an ion source 11 is set oblique to the axis B with a small angle. At the intersecting point of the two axes A and B, chopping electrodes 13 are provided. The chopping electrodes 13 are placed so that the direction of the electric field produced by the chopping electrodes 13 is nearly perpendicular to the axis A (and parallel to the plane of the drawing in FIG. 1).

A magnet 20 is provided at the chopping electrodes 13 (that is, at the intersecting point of the axes A and B). The magnet 20 can be either a permanent magnet or an electromagnet: anyway it produces a static magnetic field in the direction perpendicular to the direction of the electric field of the chopping electrodes 13 and to the axis A. The combination of the magnet 20 and the electrodes 13 constitutes a so-called Wien filter in which ions having a predetermined mass and electric charge can pass straight or deflected to a predetermined direction. In the CAICISS of the present embodiment, the electrodes 13 of the Wien filter are also used as chopping electrodes for chopping the ion beam irradiated onto the sample 17, as described later.

From the Wien filter (that is, the chopping electrodes 13 and the magnet 20) to the sample 17 along the axis B, a pair of adjusting electrodes 14, an aperture plate 15 and an ion detector 19 are provided in the CAICISS. At the intersecting point of the aperture plate 15 and the axis B, a small aperture (chopping aperture) 16 is provided for allowing ions irradiated onto the sample 17.

The operation of the CAICISS of the present embodiment is as follows. Source gas, helium gas for example, in the ion source 11 is ionized by accelerated electrons, and the ions are ejected from the ion source 11 by drawing electrodes and accelerated by accelerating electrodes along the axis A of the ion source 11. In the ion beam ejected from the ion source 11 are included thermally escaping non-ionized atoms or impurity ions having mass or electric charge different from the proper ions.

On the chopping electrodes 13 is normally applied a first voltage (actually a zero voltage), and very short pulses of a second voltage (chopping pulses) are periodically applied by the chopping controller 81. While the first voltage is applied (or no voltage is applied) on the chopping electrodes 13, all the ions (including impurity ions) ejected from the ion source 11 and flying along the axis A are deflected upward as shown by the arrow C by the magnetic field produced by the magnet 20, and no ion is irradiated onto the sample 17. While the second voltage is applied (that is, within the chopping pulses), an electric field is produced by the chopping electrodes 13 in the same space as the magnetic field produced by the magnet 20. The direction of the electric field is perpendicular to the magnetic field and to the axis A, and the magnitude of the electric field is set to balance the magnetic field so that only proper ions having a predetermined mass and electric charge are deflected to the axis B and pass through the chopping aperture 16. But impurity ions having different masses or electric charges are deflected otherwise and prevented by the aperture plate 15 from irradiating the sample 17.

In any case (that is, while chopping pulses are applied and while they are not applied), non-ionized atoms are unaffected by the magnetic field and the electric field and go straight along the axis A. Thus only the proper ions are intermittently irradiated onto the sample 17 and impurities are prevented by the aperture plate 15. The adjusting electrodes 14 finely adjusts the direction of the ion beam to the chopping aperture 16.

The irradiated ions collide with the atoms of the sample 17 mostly in its surface and scatter in every direction. Among the scattered ions, those scattered backward (backward to the direction of the incident ions) 18 are detected by the ion detector 19 placed behind the aperture plate 15. The ion detector 19 (such as a micro-channel plate) generates an arrival signal when a back-scattered ion 18 arrives, and the arrival signal is transmitted to a timer 82 via an amplifier (AMP) 83. The timer 82 starts counting clock pulses at the fall-down (or rise-up) edge of a chopping pulse generated by the chopping controller 81 and finishes counting when an arrival signal comes. Thus the timer 82 measures the time for which an ion flies from the chopping electrodes 13 to the ion detector 19 via the sample surface. The data of time of flight is sent to a main controller 84, where the flight time data are collected for many chopping pulses. Since the flight time varies with the speed of the back-scattered ions 18, the energy spectrum of the back-scattered ions 18 can be obtained by collecting the flight time data. The main controller 84 derives information of the sample surface from the energy spectrum obtained. Since noises due to impurity ions or non-ionized atoms are not included in the collected data, the accuracy and sensitivity of the measurement is enhanced in this embodiment.

The second embodiment of the present invention is now described referring to FIG. 2, in which same components have the same numerals as in FIG. 1. In the present embodiment also, the axis A of the ion source 11 is set oblique to the axis B of the ion irradiation onto the sample 17, but the Wien filter is not used. Instead, a pair of deflecting electrodes 12 is provided separately before the chopping electrodes 13 to separate nonionized atoms from the proper ions. Thus the operation of the CAICISS of the present embodiment is as follows.

A constant voltage is applied on the deflecting electrodes 12 to produce a predetermined electric field so that only ions having a predetermined mass and electric charge are deflected from the axis A to the axis B. Electrically neutral non-ionized atoms included in the ions from the ion source 11 are unaffected by the electric field of the deflecting electrodes 12 and go straight along the axis A. Ions having different mass or different electric charge are deflected by the deflecting electrodes 12, but the deflected course is different from the axis B. In any case, such impurities are prevented by the aperture plate 15 from being irradiated onto the sample 17.

In the CAICISS of the present embodiment, a certain voltage (first voltage) is normally applied on the chopping electrodes 13 by the chopping controller 81 to deflect the ions again, whereby the ions are prevented from passing through the chopping aperture 16. Very short pulses (chopping pulses) of a second voltage (which may be a zero voltage) are periodically applied on the chopping electrodes 13. The ions from the deflecting electrodes 12 can pass through the chopping aperture 16 only while the second voltage is applied, whereby the ions are intermittently irradiated onto the sample 17. After the ions are irradiated onto the sample 17, the operation is similar to that of the first embodiment.

In the present embodiment, a magnet (permanent magnet or electromagnet) may be used instead of the deflecting electrodes 12 because a magnetic field directed perpendicularly to the electric field exerts force in the same direction on a moving electric charge. A combination of electrodes and a magnet may also be used.

What is claimed is:

1. An ion scattering spectrometer for irradiating ions intermittently onto a sample and measuring the energy of ions scattered backward by the sample, the ion scattering spectrometer comprising:
   a) an ion source for ejecting ions on a first axis;
   b) a Wien filter placed on the first axis and including a pair of electrodes for producing an electric field with the direction non-parallel to the first axis and a magnet for producing a magnetic field with the direction non-parallel to the first axis and to the direction of the electric field;

c) a chopping controller for intermittently adjusting the electric field and/or the magnetic field to deflect the ions from the first axis to a second axis; and d) an aperture plate placed on the second axis between the Wien filter and the sample, and having an aperture at the intersection of the aperture plate and the second axis, whereby the ions are intermittently irradiated onto the sample and otherwise prevented by the aperture plate.

2. The ion scattering spectrometer according to claim 1, where the ion scattering spectrometer further comprises:

e) a detector for detecting ions scattered backward by the sample; and f) a timer for measuring the time for which the ions fly from the Wien filter to the detector.

3. The ion scattering spectrometer according to claim 2, where the magnet is a permanent magnet.

4. The ion scattering spectrometer according to claim 2, where the magnet is an electromagnet.

5. An ion scattering spectrometer for irradiating ions onto a sample and measuring the energy of ions scattered backward by the sample, the ion scattering spectrometer comprising:

a) an ion source for ejecting ions along a first axis;

b) a deflector for deflecting ions having a predetermined mass and electric charge toward a second axis which intersects the first axis;

c) an aperture plate placed intersecting the second axis and having an aperture at the intersecting point for allowing the ions deflected by the deflector to be irradiated onto the sample and preventing other ions;

d) a pair of chopping electrodes for intermittently allowing the ions to pass through the aperture;

e) a detector for detecting ions scattered backward by the sample; and f) a timer for measuring the time for which the ions fly from the chopping electrodes to the detector.

6. The ion scattering spectrometer according to claim 5, where the deflector is a pair of electrodes for producing an electric field with the direction non-parallel to the first axis.

7. The ion scattering spectrometer according to claim 5, where the deflector is a magnet for producing a magnetic field with the direction non-parallel to the first axis.

8. The ion scattering spectrometer according to claim 5, where the deflector is a combination of a pair of electrodes for producing an electric field with the direction non-parallel to the first axis and a magnet for producing a magnetic field with the direction non-parallel to the electric field and the first axis.

* * * * *